United States Patent [19]
Kroll et al.

[11] Patent Number: 5,925,066
[45] Date of Patent: Jul. 20, 1999

[54] ATRIAL ARRYTHMIA SENSOR WITH DRUG AND ELECTRICAL THERAPY CONTROL APPARATUS

[75] Inventors: Kai Kroll; Mark W. Kroll, both of Minnetonka, Minn.

[73] Assignee: Galvani, Ltd., Minneapolis, Minn.

[21] Appl. No.: 08/931,233

[22] Filed: Sep. 15, 1997

Related U.S. Application Data

[63] Continuation of application No. 08/549,982, Oct. 26, 1995., abandoned

[51] Int. Cl.[6] .................................................. A61N 1/365
[52] U.S. Cl. .................................................. 607/3; 607/14
[58] Field of Search ................................ 607/3, 4, 5, 14, 607/120; 604/20, 21

[56] References Cited

U.S. PATENT DOCUMENTS

| | | |
|---|---|---|
| 3,923,060 | 12/1975 | Ellinwood . |
| 3,952,750 | 4/1976 | Mirowski et al. . |
| 4,003,379 | 1/1977 | Ellinwood . |
| 4,146,029 | 3/1979 | Ellinwood . |
| 4,552,561 | 11/1985 | Eckenhoff et al. . |
| 4,572,191 | 2/1986 | Mirowski et al. . |
| 4,969,873 | 11/1990 | Steinbach et al. . |
| 5,041,107 | 8/1991 | Heil . |
| 5,087,243 | 2/1992 | Avitall ..................... 607/120 |
| 5,207,219 | 5/1993 | Adams et al. . |
| 5,220,917 | 6/1993 | Cammilli et al. . |
| 5,265,600 | 11/1993 | Adams et al. . |
| 5,282,837 | 2/1994 | Adams et al. . |
| 5,305,745 | 4/1994 | Zacouto . |
| 5,330,505 | 7/1994 | Cohen ..................... 607/3 |
| 5,350,402 | 9/1994 | Infinger et al. . |
| 5,376,103 | 12/1994 | Anderson et al. ............. 607/5 |
| 5,391,185 | 2/1995 | Kroll . |
| 5,411,524 | 5/1995 | Rahul . |
| 5,499,971 | 3/1996 | Shapland et al. ........... 604/21 |
| 5,527,344 | 6/1996 | Arzbaecher et al. ........ 607/3 |
| 5,634,899 | 6/1997 | Shapland et al. ........... 604/53 |
| 5,662,689 | 9/1997 | Elsberry et al. ............ 607/5 |

*Primary Examiner*—William E. Kamm
*Assistant Examiner*—Kennedy J. Schaetzle
*Attorney, Agent, or Firm*—Patterson & Keough, P.A.

[57] ABSTRACT

An atrial arrythmia sensor and drug dispensing apparatus is disclosed. The apparatus comprises a multiphase, multistage intelligent system to monitor and treat atrial fibrillation. The apparatus includes atrial rate sensing means, cardiac pacing and antitachycardia pacing means, drug delivery means including a self-cleaning catheter line with multi-drug dispensing capability preferably operated using a dual pump arrangement and an iontophoretic device. The drug delivery system may also include a porous catheter to discharge drug into the atrium. The intelligent system includes a memory implemented logic (software) to continuously monitor the atrial rate and initiate a response of either cardiac pacing, antitachycardia pacing or drug dispensing based on preset cardiac activity parameters. The system also includes a medical history recording feature.

6 Claims, 3 Drawing Sheets

ATRIAL ARRYTHMIA SENSOR WITH DRUG AND ELECTRICAL THERAPY CONTROL APPARATUS

This is a Continuation of application Ser. No. 08/549,982 filed Oct. 26, 1995, now abandoned.

FIELD OF THE INVENTION

This invention generally relates to atrial drug delivery apparatus. Specifically, the invention pertains to the treatment of atrial fibrillation, to enable a direct intervention utilizing a self cleaning single or multiple drug delivery system or an iontophoretic device, in cardiac arrythmia patients. More specifically, the present invention discloses an accurate atrial fibrillation sensor, a pacer, integrated with the sensor for maintaining heart beats at predetermined normal beats per minute (BPM) and also to trigger antitachycardia pacing above a preset BPM, and a drug delivery regiment to normalize heart beats within preset limits.

BACKGROUND OF THE INVENTION

Atrial fibrillation is a common occurrence in cardiac patients. It is generally caused by the lack of blood output from the atria and usually leads to blood clots in the atria. The blood clots may lodge in either the lungs or the brain resulting in serious health problems, strokes or possibly death to the patient.

Various types of oral drugs have been tried to treat atrial fibrillation. While some patients are helped by these drug therapies, the majority of patients are not successfully and safely treated and require a different type of treatment. One of the most significant shortcomings of these drugs is the side effects they may have on the patients. Specifically, in some patients administration of these drugs leads to a ventricular fibrillation which is almost always immediately fatal.

Traditional prior art provides a number of devices and methods to control atrial fibrillation. Generally, the prior art discloses defibrillation systems which employ electrical shock to control atrial fibrillation. For example, U.S. Pat. No. 4,572,191 and U.S. Pat. No. 3,952,750 teach a standby electrical shock device for atrial defibrillation. Similarly, recently issued patents in this art disclose electrical shock therapy systems for atrial defibrillation. For example, U.S. Pat. No. 5,282,837, U.S. Pat. No. 5,265,600 and U.S. Pat. No. 5,391,185 disclose various embodiments relating to implantable electrical atrial defibrillator.

The use of electrical shock in the treatment of atrial fibrillation poses some hitherto unresolved problems. Primarily, electrical atrial defibrillation requires shocks in the order of one to two joules of electrical energy. This shock magnitude is very painful to the patient and is undesirable. Another significant disadvantage of electrical shock therapy is the fact that atrial defibrillation shock may lead to ventricular fibrillation. This is because a moderate level shock during the repolarization of the ventricles will typically lead to fibrillation. In order to avoid this problem the prior art utilizes methods and apparatus to sense the R-wave in the right ventricle and carefully synchronizes the atrial shock to avoid impinging upon the ventricular T-wave which would represent the repolarization of the ventricle. The risk of fibrillating the heart with an atrial defibrillation shock can also be minimized by delivering shocks which are timed with ventricular activity. This method is generally disclosed in U.S. Pat. No. 5,207,219, U.S. Pat. No. 5,350,402 and U.S. Pat. No. 5,411,524.

In spite of the advances made by the prior art, atrial defibrillation shock therapy may cause ventricular fibrillation and therefore a therapy for an otherwise non-fatal condition might be fatal to the patient. One possible solution is to incorporate a ventricular defibrillator with an atrial defibrillator. However, the energy required for ventricular defibrillation is significantly higher than is required for atrial defibrillation. Therefore, the capacitors and batteries need to be large and the device would need to be the same size as a conventional implantable cardiac ventricular defibrillator.

An alternate therapy for atrial defibrillation comprises drug injection devices. Specifically, for example, U.S. Pat. No. 3,923,060 and U.S. Pat. No. 4,146,029 disclose various types of implantable drug pumps which discharge an amount of drugs at the onset of atrial fibrillation. Similarly, U.S. Pat. No. 4,552,561 and U.S. Pat. No. 4,969,873 disclose a drug pump mounted on the outside of a patient's body for drug injection and a specialized drug chamber for a pump, respectively. Further, U.S. Pat. No. 5,041,107 discloses the use of iontophoresis for drug delivery.

Publications highlighting some of the critical limitations of the prior art and the need for alternate solutions include an article by Bloem et al., *Journal of Electrocardiology* Vol. 26 Supp. 1994, p. 60. This article suggests the use of implantable drug for atrial defibrillation. Further, the use of drugs for ventricular defibrillation is generally disclosed in U.S. Pat. No. 5,220,917 by Cammilli, et al., and in a publication in *New Trends and Arrhythmias* Vol. 8, No, 4 of 1992 in an article by Cammilli, et al., entitled "Immediate Ventricular Defibrillation by Automatically Retroinfused Drug and Coronary Sinus During Experimental Acute Myocardial Infraction in Swine". Similarly, the use of drugs in ventricular defibrillation is also disclosed in "Implantable Pharmacological Defibrillator (AI PhD): Preliminary Investigation in Animals" by Cammilli et al., published in *Pace* February 1991, Vol. 14. Further, in U.S. Pat. No. 5,305,745 Zacouto teaches the use of implantable injector of thrombolytic agents to break clots.

While prior art methods and devices have performed adequately, there is an acute need for a reliable means to control and manage atrial fibrillation without the problems and limitations associated with external or implantable electrical shock therapy. Accordingly, as will be set forth below, the present invention overcomes these and related limitations of the prior art. Specifically, the present invention utilizes a system and device for atrial defibrillation through the implementation of, inter alia, a self cleaning single/multiple drug delivery system, a cardiac pace monitoring and control system, antitachycardia pacing system, and a therapeutic and cardiac activity history recording and maintenance system.

SUMMARY OF THE INVENTION

The present invention provides a multiphase integrated system to treat actual and/or cardiac conditions which potentially result in atrial fibrillation. Generally, the present invention enables drug delivery into the atrium of the heart upon sensing the onset and/or imminence of an atrial fibrillation. The drug delivery system includes preferably a dual pump device which promotes the delivery of multiple drugs needing to be segregated before mixing for delivery. In the alternate, an iontophoretic drug delivery system is implemented. Further, the preferred dual pump device enables hygienic maintenance of drug delivery catheters by flushing the lines with cleaning fluid at pre-delivery. Furthermore, the present invention incorporates a pacer to pace the heart beat and retain it within predetermined beat rates when the beat rate is lower than 60 beats per minute (BPM). Furthermore, if the BPM exceeds 180 BPM an antitachycardia pacing is activated. In the event that the antitachycardia pacing attempt fails to restore the heart rate to under 180 BPM, the drug delivery system is initiated to dispense a measured amount of drug. The system then monitors the BPM for at least three minutes and repeats the drug delivery until a heart rate of less than 180 BPM is registered. The system counts the number of consecutive drug delivery events and reverts back to performing antitachycardia pacing procedures followed by drug delivery as apparent. The system also includes a memory system which records cardiac history, events and types of drugs delivered as well as related medical history.

Accordingly, the present invention is a multiphase, multistage intelligent system to monitor and treat atrial fibrillation. Moreover, the present invention provides a comprehensive system and device for atrial defibrillation and uniquely combines an efficient and reliable sensing and pacing system to prevent and therapeutically manage atrial fibrillation.

DESCRIPTION OF THE PREFERRED EMBODIMENT

Figure 1:
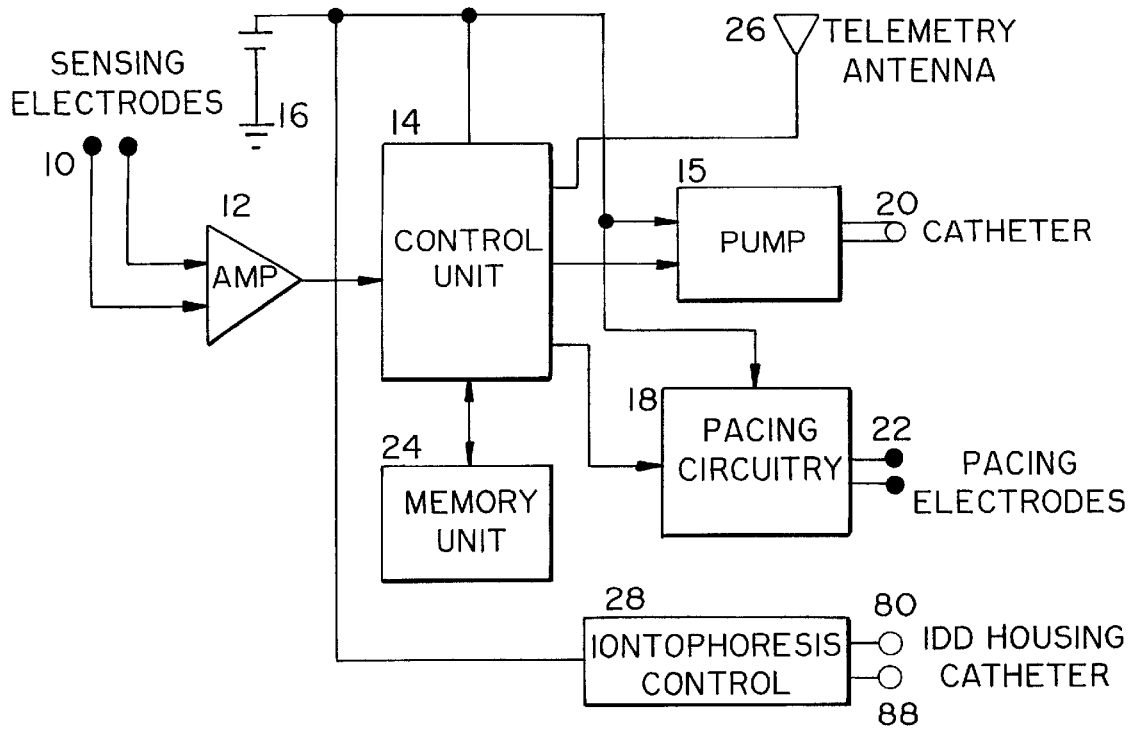
FIG. 1 is a block diagram representing a schematic layout of the significant components of the invention and their structural and operational communications thereof.

Referring now to the drawings, FIG. 1 shows a schematic layout of the most important components of the invention comprising the device which is implantable in a human body.

Sensing electrodes 10 are placed in the atrium for detecting the atrial rate. These electrodes provide the atrial electrogram signal which is then fed into amplifier 12. The output of amplifier 12 is provided to the control unit 14. Battery 16 provides electrical power to the control unit 14 and to a pump 15 and to pacing circuitry 18 as well as to all electrical components in the device. When a high rate is sensed which is suggestive of atrial fibrillation then the control unit 14 will instruct the pump 15 to inject appropriate quantity of drug into the atria through catheter 20. Catheter 20 may be porous. Whether porous or otherwise, catheter 20 may be initiated to deliver antiarrhythmic drugs into the atrium by control unit 15 and the processor memory unit 24. Examples of drugs that can defibrillate the atria are amiodarone, bethanidine, clofilium, encainide, esmolol, flecainide, ibutilide, Org 7797, phenotiazine derivatives, procainamide, propafenone, quinidine, quinidine with digitalis, quinidine with isoptin, quinidine with verapamil, sotalol, tricyclic anti-depressants, and verapamil. Some of these drugs will be more suitable than others as they have more stability at the body temperature of 37 degrees celsius.

The control unit 14 is also capable of instructing the pacing circuitry 18 to deliver pacing pulses, should they be necessary, through pacing electrodes 22. The pacing electrodes 22 could, in one embodiment, be identical to the sensing electrodes 10.

Figure 3:
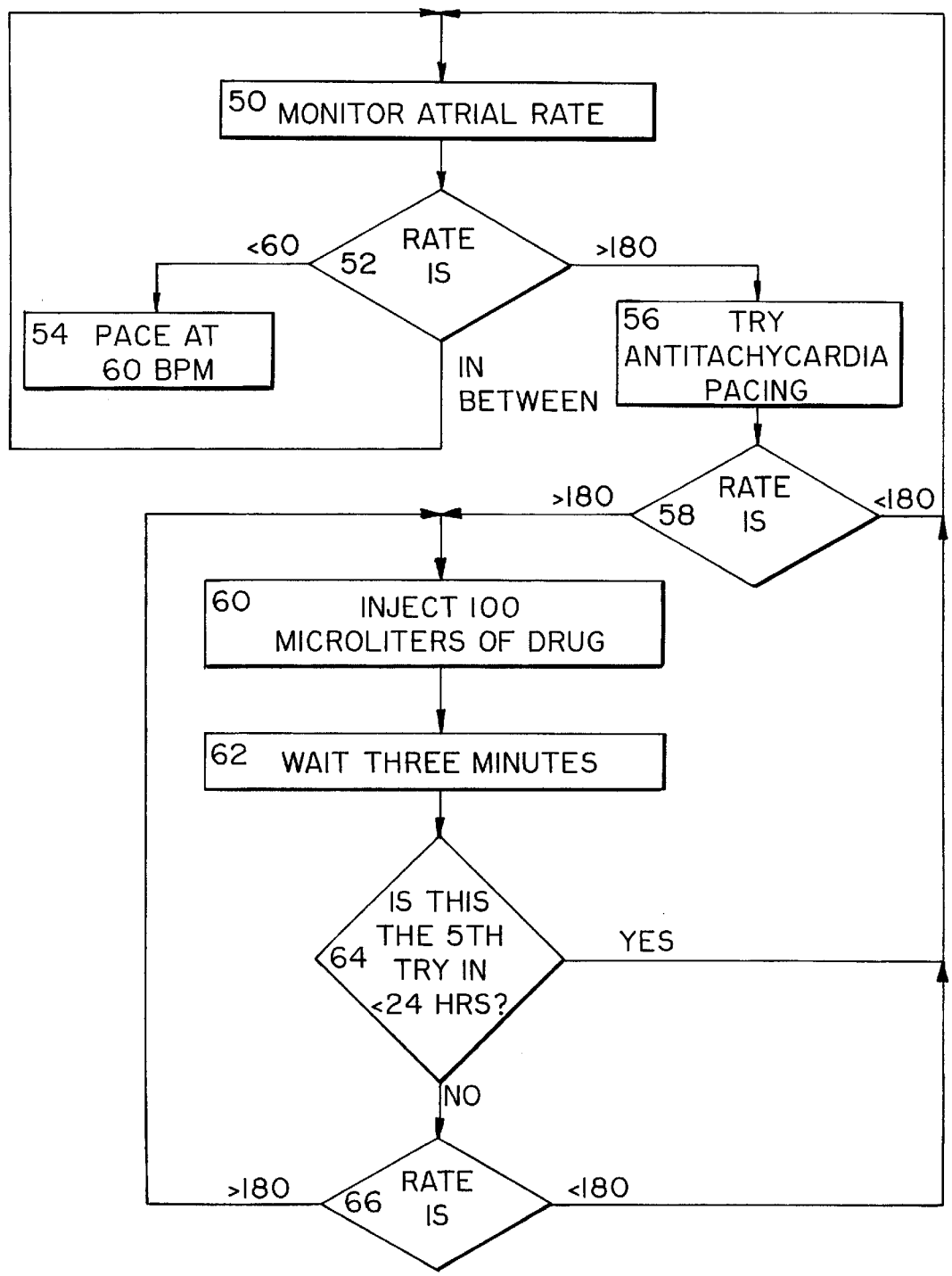
FIG. 3 is a flow chart of the microprocessor logic and the preferred operational sequence of the present invention.

Iontophoresis control 28 is also powered by battery 16 and provides a current between the IDD housing 80 (FIG. 3) and the catheter 88 (FIG. 3).

The control unit 14 via memory unit 24 will also store the complete history of the patient therapy. This can include the electrograms from the sensing electrodes for later analysis. These electrograms will be stored and stamped with the time for later uplink to a programmer for analysis. The therapy history including rhythms detected, drugs delivered, pacing performed, and cardiac response can be stored along with the time of their occurrence for later uplink. When a request for uplink is received by the control unit 14 through telemetry antenna 26 then the control unit will deliver this information from the memory unit 24 to the telemetry antenna 26.

Figure 2:
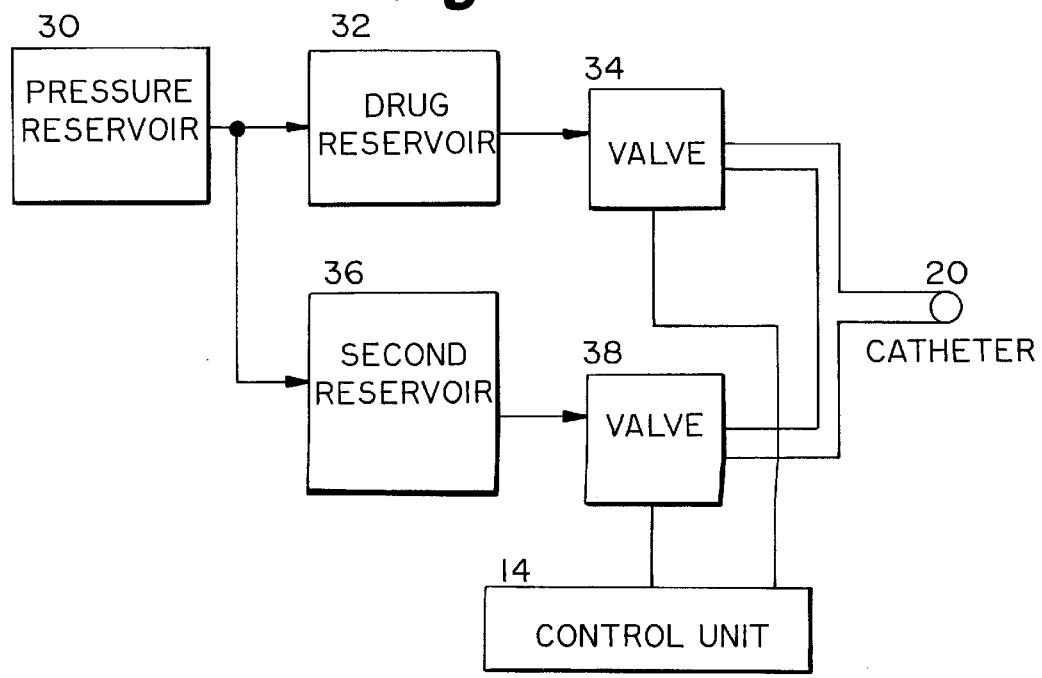
FIG. 2 is a block diagram of the present invention showing a detail schematics of the pump and single/multiple drug delivery system.

FIG. 2 shows an alternative embodiment for the drug pump. In this case a pressure reservoir 30 is in contact with a main drug reservoir 32 to provide pressure against the drug reservoir. A valve 34 is controlled by control unit 14. When the control unit 14 instructs the valve to deliver an amount of drug to the heart then the pressure from the reservoir 30 acting on the main drug reservoir 32 will force an amount of drugs through the valve 34 and thence into the catheter 20 for ultimate delivery to the heart.

In yet another alternative embodiment a second agent reservoir 36 receives pressure from the pressure reservoir 30 and thence is able to deliver its agent through valve 38 and thence to catheter 20. The second agent could be, in one embodiment, a flushing agent to clean the catheter in advance of the delivery of the drug. This could be necessary because of clotting and contamination of the catheter after a long period of inactivity in the human body. In the alternative, the second agent reservoir could be used to store an auxiliary drug. For example when the earlier combination such as quinidine with verapamil was mentioned and quinidine could be stored in the main drug reservoir and verapamil could be stored in the second agent reservoir.

Referring now to FIG. 3, a detail schematics of the logic/program and the preferred operational sequence/process of the present invention is shown. The operational sequence is initiated at logic step 50 where the atrial rate of the patient's heart beat is monitored. The program implemented in memory unit 24 interfaces with control unit 14 (see FIG. 1) and, inter alia, coordinates the sequential operation of the systems of the present invention. Accordingly, the operational sequence implemented by the program proceeds to decision block 52 where the atrial rate monitored at logic step 50 is analyzed and classified in accordance with predetermined heart beat parameters. If the BPM is less the 60 BPM the logic proceeds to logic step 54 where a pacer is initiated to restore the BPM up to 60 BPM. In the alternate if the heart beat is greater than 180 BPM the logic proceeds to logic step 56 where antitachycardia pacing is initiated to bring the BPM below 180 BPM. Further, when the BPM is found to be greater than 60 BPM but less than 180 BPM, the logic reverts back to logic step 50 and maintains a vigil of monitoring the atrial rate.

The results of the antitachycardia pacing under logic step 56 are monitored under decision block 58. In the event that the antitachycardia pacing controls the BPM to stay under 180 BPM, the logic reverts back to logic step 50 and resumes monitoring the atrial rate. In the alternate, if the antitachycardia pacing is unsuccessful in bringing the BPM below 180 BPM, the sequence proceeds to logic step 60 where at least 100 microliters of drug is injected into the atrium of the patient. The system then waits for three minutes under logic step 62. Subsequently, an assessment of the drug injection history and the antitachycardia pacing effect is made under decision block 64. If it is found that the last injection, pursuant to an antitachycardia pacing, is the fifth attempt to bring the BPM under 180 BPM in less than 24 hours, the logic sequence reverts back to logic step 50. However, if the finding under decision block 64 is in the negative, the logic proceeds to decision block 66 where the current BPM rate is checked. In the event the rate is found to be less than 180 BPM the logic sequence reverts back to logic step 50 and repeats the sequence as apparent. On the other hand, if the rate is greater than 180 BPM, the logic sequence reverts back to logic step 60 and operates pursuant to the subroutine thereafter.

Accordingly, the present invention utilizes a logic sequence, program or process implemented in memory unit 24 to monitor atrial rate, initiate a pacer or antitachycardia pacer and deliver drugs to the atrium.

Figure 4:
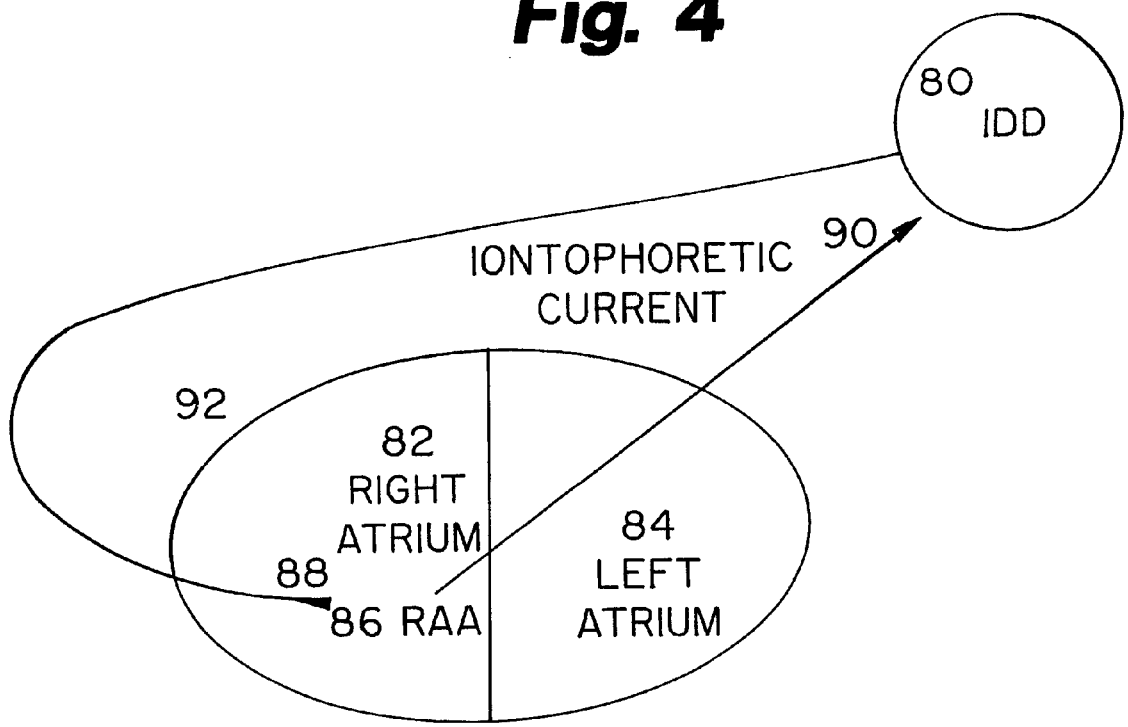
FIG. 4 shows an alternate embodiment in which the device of the present invention is implanted near the atria with an iontophoretic current for drug delivery.

FIG. 4 shows the implantable drug defibrillator (IDD) 80 implanted in the left portion of the body relative to the left atrium 84. The catheter 88 is placed within the right atrium 82 and particularly in the right atrial appendage (RAA) 86. When atrial drug defibrillation is desired then the drug is electrically pulled from the catheter 88 by an electrical current flow 90 which passes between the catheter 88 and the implantable drug defibrillator housing. Alternatively, catheter 88 could be placed in the pericardial cavity of the heart.

Having thus described the preferred embodiments of the present invention, those skilled in the art will readily appreciate the many other embodiments which can be employed within the scope of the claims provided herein below.

That which is claimed is:

1. A method for controlling atrial fibrillation using anti-tachycardia pacing and drug injection into the heart of a patient to control atrial fibrillation comprising the steps of:
   monitoring the atrial rate of a patient's heart;
   comparing the atrial rate to a threshold value to detect atrial fibrillation;
   implementing anti-tachycardia pacing when the threshold atrial rate is exceeded; and
   implementing a drug delivery regimen if said anti-tachycardia pacing is unable to control the atrial fibrillation.

2. The method according to claim 1 wherein said drug delivery regimen includes the step of applying an iontophoretic current to force drug discharge into the patient's heart.

3. An atrial arrythmia sensing, therapy control and management apparatus having a memory implemented logic sequence in which operations of the apparatus in performing the desired functions include a set of instructions formed into each of a series of operational commands to be performed, the apparatus-implemented process comprising:
   an initial atrial rate-regulating process that continuously regulates an atrial rate of a patient's heart, the initial atrial rate-regulating process comprising:
      continuous monitoring of the atrial rate;
      determining if the monitored atrial rate is less than 60 BPM;
      if the atrial rate is less than 60 BPM, implementing a first-type pacing process to increase said atrial rate to 60 BPM;
      determining if the monitored atrial rate is greater than 60 BPM;
      if the monitored atrial rate is greater than 60 BPM, ending the first-type pacing process;
      determining if the monitored atrial rate is greater than 180 BPM;
      if the atrial rate is greater than 180 BPM, implementing a second-type pacing process using anti-tachycardia pacing therapy to decrease the atrial rate to less than 180 BPM;
      determining if the monitored atrial rate is less than 180 BPM;
      if the monitored atrial rate is less than 180 BPM, ending the implementation of the second-type pacing process;
   a second atrial rate-regulating process that implements a third-type pacing process to maintain the atrial rate at less than 180 BPM if the second-type pacing process fails to maintain the atrial rate under 180 BPM, the second atrial rate-regulating process comprising:
      monitoring the second-type pacing process and comparing the second-type pacing process duration to a second-type pacing process threshold value;
      if the second-type pacing process duration exceeds the second-type pacing process threshold value, injecting an amount of drug from a drug delivery system;
      a therapy data management and comparison process in which the injections are monitored and timed so that drug injection dosages may be adjusted and so that a reversion to the initial atrial rate-regulating process is initiated if five injections are administered within 24 hours of the most recent initiation of the second atrial rate-regulating process;
      determining if the monitored atrial rate is less than 180 BPM; and
      if the monitored atrial rate is less than 180 BPM, ending the implementation of the third-type pacing process and reverting to the initial atrial rate-regulating process.

4. The apparatus of claim 3 wherein said third-type pacing process includes injecting drugs into the right atrium of the patient's heart using an iontophoresis system.

5. The apparatus of claim 3 wherein said therapy data management includes storing patient therapy information compiled from digital electrograms from a plurality of sensing electrodes, analog electrograms from said sensing electrodes, atrial rhythm records, data of delivered drugs from said drug delivery system, data of pacing shocks administered from a cardiac pacer and an antitachycardia pacer, records of cardiac responses to preceding therapies and any combination thereof.

6. The apparatus of claim 3 wherein said third-type pacing process includes initiating a self-cleaning system using flushing means to clean drug delivery catheter(s) before and after drug delivery events.

* * * * *